US00PP20464P2

(12) United States Plant Patent
Eveleens

(10) Patent No.: US PP20,464 P2
(45) Date of Patent: Nov. 10, 2009

(54) ***HYDRANGEA* PLANT NAMED 'MAGICAL EMERALD'**

(50) Latin Name: *Hydrangea macrophylla*
Varietal Denomination: Magical Emerald

(75) Inventor: Cornelis Pieter Eveleens, De Kwakel (NL)

(73) Assignee: Kolster Beheer B.V., Boskoop (NL)

( * ) Notice: Subject to any disclaimer, the term of this patent is extended or adjusted under 35 U.S.C. 154(b) by 0 days.

(21) Appl. No.: 12/221,684

(22) Filed: Aug. 4, 2008

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent L Bell
(74) *Attorney, Agent, or Firm*—C. A. Whealy

(57) ABSTRACT

A new and distinct cultivar of *Hydrangea* plant named 'Magical Emerald', characterized by its upright and mounded plant habit; strong roots and stems; freely branching habit; and large inflorescences with very light pink-colored flowers.

2 Drawing Sheets

Botanical designation: *Hydrangea macrophylla.*
Cultivar denomination: 'Magical Emerald'.

BACKGROUND OF THE INVENTION

The present invention relates to a new and distinct cultivar of *Hydrangea*, botanically known as *Hydrangea macrophylla* and hereinafter referred to by the name 'Magical Emerald'.

The new *Hydrangea* is a product of a planned breeding program conducted by the Inventor in Aalsmeer, The Netherlands. The objective of the breeding program was to create new *Hydrangea* cultivars with strong stems, large inflorescences and attractive flower color.

The new *Hydrangea* originated from a cross-pollination made by the Inventor in 2002 in Aalsmeer, The Netherlands, of two unnamed seedling selections of *Hydrangea macrophylla*, not patented. The new *Hydrangea* was discovered and selected by the Inventor as a single flowering plant within the progeny of the stated cross-pollination in a controlled greenhouse environment in Aalsmeer, The Netherlands in 2004.

Asexual reproduction of the new *Hydrangea* by vegetative cuttings in a controlled greenhouse environment in Aalsmeer, The Netherlands since 2004, has shown that the unique features of this new *Hydrangea* are stable and reproduced true to type in successive generations.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Magical Emerald'. These characteristics in combination distinguish 'Magical Emerald' as a new and distinct cultivar of *Hydrangea:*

1. Upright and mounded plant habit.
2. Strong roots and stems.
3. Freely branching habit.
4. Large inflorescences with very light pink-colored flowers.

Plants of the new *Hydrangea* differ from plants of the parent selections primarily in plant habit as plants of the new *Hydrangea* are more uniform than plants of the parent selections. In addition, plants of the new *Hydrangea* have larger flowers than plants of the parent selections.

Plants of the new *Hydrangea* can be compared to plants of *Hydrangea* 'Snowball', not patented. Plants of the new *Hydrangea* differ from plants of 'Snowball' primarily in flower color as plants of 'Snowball' have pure white-colored flowers.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color value cited in the detailed botanical description which accurately describe the colors of the new *Hydrangea.*

The photograph on the first sheet comprises a side perspective view of a typical flowering plant of 'Magical Emerald' grown in a container.

The photograph at the top of the second sheet is a close-up view of a typical inflorescence of 'Magical Emerald'.

The photograph at the bottom of the second sheet is a close-up view of typical leaves of 'Magical Emerald'.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photographs and in the following description were grown during the spring in Boskoop, The Netherlands, in containers in a glass-covered greenhouse and under conditions which closely approximate commercial production conditions. During the production of the plants, day temperatures ranged from 15° C. to 20° C. and night temperatures ranged from 14° C. to 15° C. Plants of the new *Hydrangea* were pinched one time and had been planted for two years when the photographs and description were taken.

Botanical description: *Hydrangea macrophylla* 'Magical Emerald'.

Parentage:

*Female, or seed, parent.*—Unnamed seedling selection of *Hydrangea macrophylla*, not patented.

*Male, or pollen, parent.*—Unnamed seedling selection of *Hydrangea macrophylla*, not patented.

Propagation:

*Method.*—By cuttings.

*Time to initiate roots, summer.*—About 20 days at temperatures of 17° C. to 25° C.

*Time to initiate roots, winter.*—About 30 days at temperatures of 10° C. to 15° C.

*Time to produce a rooted young plant, summer.*—About 40 days at temperatures of 17° C. to 25° C.

*Time to produce a rooted young plant, winter.*—About 70 days at temperatures of 10° C. to 15° C.

*Root description.*—Medium in thickness, fibrous; creamy brown in color.

*Rooting habit.*—Freely branching; moderately dense.

Plant description:

*Form/growth habit.*—Upright and mounded plant habit; broad inverted triangle. Strong lateral branches; moderately vigorous growth habit.

*Plant height.*—About 33.7 cm.

*Plant diameter or area of spread.*—About 57.4 cm.

*Branching habit.*—Freely branching with about seven lateral branches per plant; pinching enhances lateral branch development.

*Lateral branches.*—Length: About 23.8 cm. Diameter: About 6.5 mm. Internode length: About 6.5 cm. Texture: Smooth, glabrous. Strength: Strong. Color: Close to 144A.

Foliage description:

*Arrangement.*—Opposite, simple.

*Length.*—About 14.8 cm.

*Width.*—About 9.1 cm.

*Shape.*—Broadly oval to broadly elliptic.

*Apex.*—Acute to apiculate.

*Base.*—Attenuate.

*Margin.*—Serrate.

*Texture, upper and lower surfaces.*—Smooth, glabrous.

Venation pattern.—Pinnate.

*Color.*—Developing leaves, upper surface: Close to 143A. Developing leaves, lower surface: Close to 146B. Fully expanded leaves, upper surface: Between 137A and 147A; venation, close to 145B to 145C. Fully expanded leaves, lower surface: Between 138A and 147B; venation, between 144C and 145A.

*Petiole.*—Length: About 3.1 cm. Diameter: About 4.5 mm. Texture, upper and lower surfaces: Smooth, glabrous. Color, upper and lower surfaces: Close to 144A to 144B.

Flower description:

*Flower type and habit.*—Single fertile and sterile flowers arranged on terminal panicles; panicles large, flattened and globular. Flowers face upright to outward. Flowers not fragrant.

*Natural flowering season.*—Continuous flowering from early April until October in The Netherlands.

*Flower longevity.*—Flowers maintain good substance and color for about four weeks on the plant. Flowers persistent.

*Quantity of flowers.*—Freely flowering habit; about 28 fertile flowers and about 100 sterile flowers per panicle.

*Panicle height.*—About 10.5 cm.

*Panicle diameter.*—About 17.1 cm.

*Fertile flower diameter.*—About 1.2 cm.

*Fertile flower depth (height).*—About 7 mm.

*Sterile flower diameter.*—About 6 cm.

*Sterile flower depth (height).*—About 2 cm.

*Flower buds.*—Length: About 5 mm. Diameter: About 4 mm. Shape: Globular. Color: Close to 75B to 75C.

*Petals, present on fertile flowers only.*—Arrangement: About five in a single whorl. Length: About 5 mm. Width: About 3 mm. Shape: Ovate. Apex: Acute. Base: Attenuate. Margin: Entire. Texture, upper and lower surfaces: Smooth, glabrous. Color: When opening, upper surface: Close to 68A. When opening, lower surface: Close to 65A. Fully opened, upper surface: Close to 68B. Fully opened, lower surface: Close to 65B.

*Sepals, fertile flowers.*—Quantity per flower: About five in a single whorl. Length: About 3 mm. Width: About 1.5 cm. Shape: Ovate. Apex: Acute. Base: Cuneate. Margin: Entire. Texture, upper and lower surfaces: Smooth, glabrous. Color, immature, upper and lower surfaces: Close to 145D. Color, mature, upper and lower surfaces: Close to 150D.

*Sepals, sterile flowers.*—Quantity per flower: About four in a single whorl. Length: About 3.2 cm. Width: About 4.4 cm. Shape: Roughly reniform. Apex: Rounded to bluntly acute; emarginate. Base: Cuneate. Margin: Serrate to crenate. Texture, upper and lower surfaces: Smooth, glabrous. Color, immature, upper and lower surfaces: Close to 157A. Color, mature, upper and lower surfaces: Close to N155D flushed with close to 69C to 69D.

*Pedicels, fertile flowers.*—Angle: About 10° from vertical. Strength: Moderately strong. Length: About 5 mm. Diameter: About 1 mm. Texture: Smooth, glabrous. Color: Close to 65C to 65D.

*Pedicels, sterile flowers.*—Angle: About 55° from vertical. Strength: Moderately strong. Length: About 3.7 cm. Diameter: About 2 mm. Texture: Smooth, glabrous. Color: Close to 65C to 65D.

*Reproductive organs, present on fertile flowers only.*—Stamens: Quantity per flower: About ten. Filament length: About 4 mm. Filament color: Close to 68B. Anther shape: Reniform. Anther length: About 1.5 mm. Anther color: Close to 186D. Pollen amount: Moderate to abundant. Pollen color: Close to 156D. Pistils: Pistil quantity per flower: About three. Pistil length: About 1 mm. Stigma shape: Club-shaped. Stigma color: Close to 70B. Style length: About 0.7 mm. Style color: Close to 68D. Ovary color: Close to 68D.

*Fruits/seeds.*—Fruit and seed development have not been observed on plants of the new *Hydrangea*.

Disease/pest resistance: Plants of the new *Hydrangea* have been observed to be relatively resistant to Powdery Mildew; plants of the new *Hydrangea* have not been observed to be resistant to pests or other pathogens common to *Hydrangea*.

Temperature tolerance: Plants of the new *Hydrangea* have been shown to be tolerant to temperatures ranging from about −15° C. to about 30° C.

It is claimed:

1. A new and distinct *Hydrangea* plant named 'Magical Emerald' as illustrated and described.

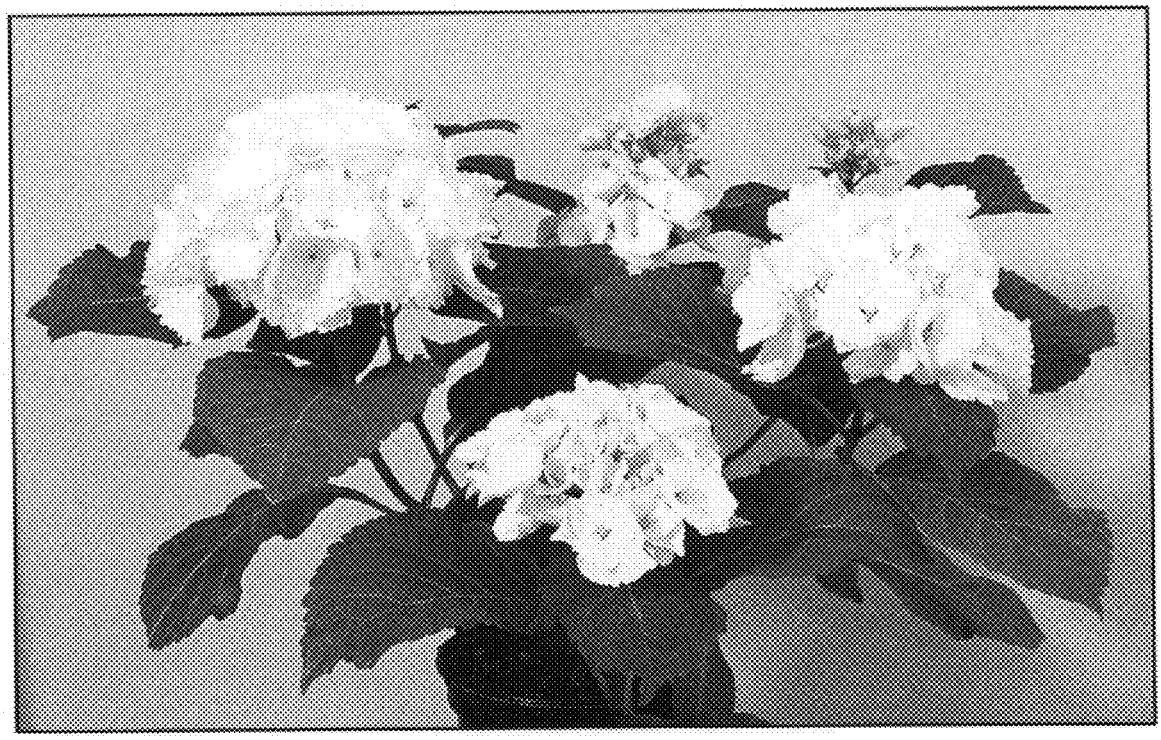

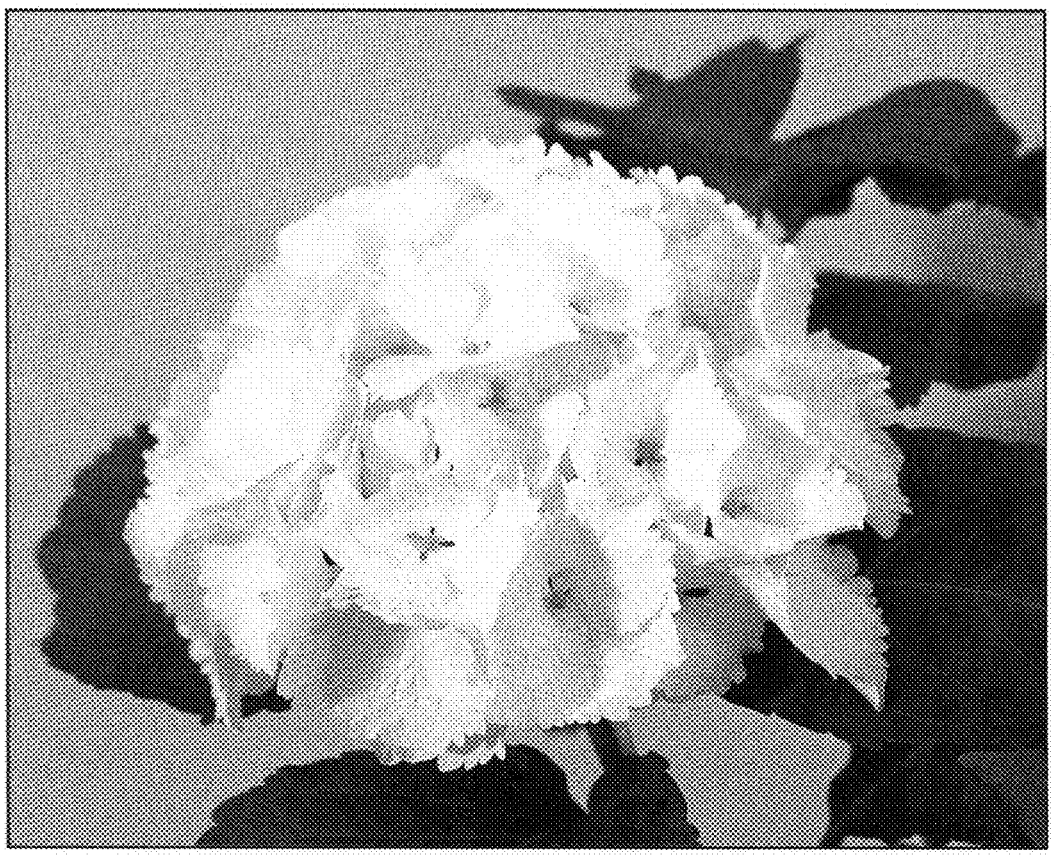
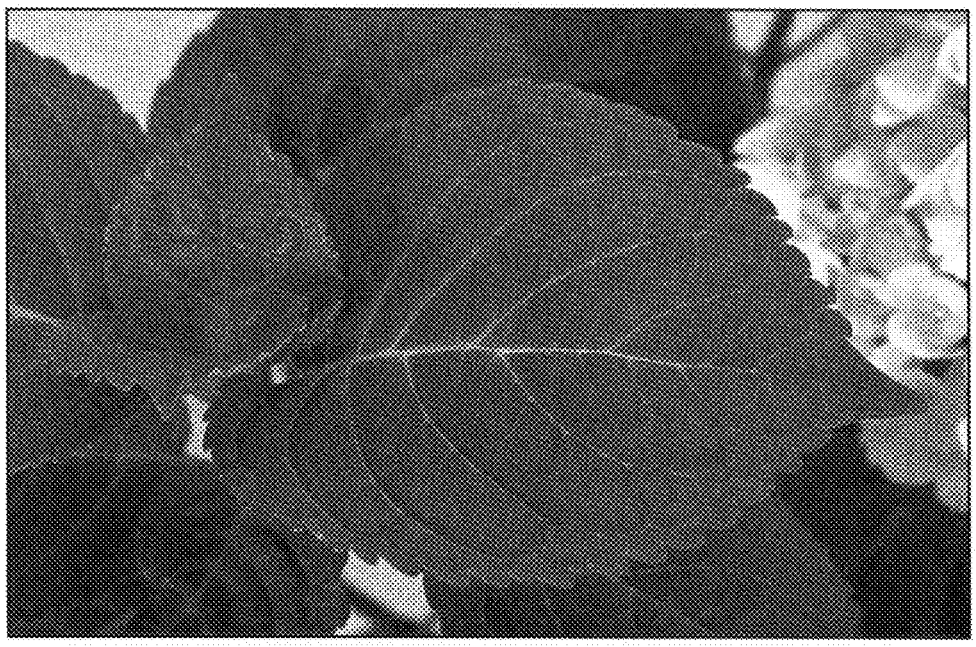

* * * * *